(12) United States Patent
Larsson et al.

(10) Patent No.: US 6,347,542 B1
(45) Date of Patent: *Feb. 19, 2002

(54) METHOD AND ARRANGEMENT FOR NON-DESTRUCTIVE DETERMINATION OF THE PROPERTIES OF AN OBJECT

(75) Inventors: Daniel Larsson, Göteborg; Sven Ohlsson, Partille; Mikael Perstorper, Mölndal, all of (SE)

(73) Assignee: Dynalyze AB, Partille (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/202,535
(22) PCT Filed: Jun. 17, 1997
(86) PCT No.: PCT/SE97/01090
§ 371 Date: Dec. 16, 1998
§ 102(e) Date: Dec. 16, 1998
(87) PCT Pub. No.: WO98/01737
PCT Pub. Date: Jan. 15, 1998

(30) Foreign Application Priority Data

Jun. 17, 1996 (SE) .............................................. 9602374

(51) Int. Cl.[7] .............................. G01M 7/08; G01N 3/30
(52) U.S. Cl. ........................ 73/12.12; 73/12.09; 73/579
(58) Field of Search ........................... 73/12.01, 12.09, 73/12.12, 573, 579, 580, 581, 582, 583

(56) References Cited

U.S. PATENT DOCUMENTS

| | | |
|---|---|---|
| 2,102,614 A | 12/1937 | Couch |
| 2,486,984 A | 11/1949 | Rowe |
| 4,399,701 A | 8/1983 | Dunlop ........................ 73/579 |
| 4,446,733 A | 5/1984 | Okubo ......................... 73/579 |
| 4,722,223 A * | 2/1988 | Bach et al. .................... 73/579 |
| 4,852,029 A * | 7/1989 | Pope et al. ................... 364/556 |
| 4,858,469 A * | 8/1989 | Hosgood et al. ............... 73/579 |
| 4,926,691 A | 5/1990 | Franklin et al. ............... 73/579 |
| 5,060,516 A | 10/1991 | Lau et al. ..................... 73/602 |
| 5,207,100 A | 5/1993 | Striffler |
| 5,255,565 A | 10/1993 | Judd et al. |
| 5,515,730 A * | 5/1996 | Manzouri ..................... 73/655 |
| 5,520,052 A * | 5/1996 | Pechersky .................... 73/579 |
| 5,533,399 A * | 7/1996 | Gibson et al. ................. 73/579 |
| 5,621,172 A * | 4/1997 | Wilson et al. ................. 73/579 |
| 5,841,030 A * | 11/1998 | Honsberg et al. .............. 73/579 |

FOREIGN PATENT DOCUMENTS

| | | |
|---|---|---|
| DE | 4435975 | 4/1995 |
| GB | 1 244 699 | 9/1971 |
| SE | 348558 | 9/1972 |

OTHER PUBLICATIONS

"Strength and stiffness prediction of timber using conventional and dynamic methods" Perstorper, First European Symposium on Nondestructive Evaluation of Wood, University of Sopron, Hungary, Sep. 21–23, 1994, vol. 2.

* cited by examiner

Primary Examiner—Hezron Williams
Assistant Examiner—Rose M. Miller
(74) Attorney, Agent, or Firm—Venable; Robert J. Frank (57) ABSTRACT

A method and arrangement for the nondestructive determination of a property of an object including a conveyer for movably supporting the object. A testing unit, including a movable member and a stroking body, is mounted adjacent the conveyer. The conveyer moves the object into and then out of engagement with the movable member. When the object is out of engagement with the movable member, it is physically impacted by the stroking body causing the object to freely vibrate at at least one natural resonant frequency mode. A detector detects the vibration of the object resulting from the physical impact on the object by the stroking body. A computer coupled to the detector processes the detector output and determines the properties of the object.

24 Claims, 5 Drawing Sheets

METHOD AND ARRANGEMENT FOR NON-DESTRUCTIVE DETERMINATION OF THE PROPERTIES OF AN OBJECT

TECHNICAL FIELD

The present invention relates to a method and an arrangement for non-destructive determination of rigidity, tensile and/or structural properties of a preferably oblong and/or plate-shaped object. Determination of the geometrical dimensions of the object are obtained through impact excitation and registration of resonance frequencies of natural modes of the object.

The invention also relates to an assembly including an arrangement according to the invention.

BACKGROUND OF THE INVENTION

When constructional wood is mechanically strength sorted, classification is generally based on evaluations of the coefficient of elasticity of the wood by applying a static bend load in a pliable direction. This coefficient of elasticity is correlated with the strength of the wood and forms the basis for sorting into strength classes. However, these machines have limited performance and do not have sufficient capacity to characterize high strength wood. The majority of conventional sorting machines require that the wood be transported longitudinally through the machine, while in most cases it would be advantageous, from the production technique point of view, if the machines could manage to perform classification during the continuous cross convey of the wood.

In the laboratory environment, methods based on the measurement of fundamental resonance frequencies at bending and axial vibration, respectively, have been shown to be considerably more accurate than conventional machines for predicting bending strength, as discussed in "Strength and stiffness prediction of timber using conventional and dynamic methods," by Mikael Perstorper, First European Colloquiums on Non-destructive Evaluation of Wood, University of Sopron, Hungary, Sep. 21–23, 1994, vol. 2. The problem with this method is that until now adoption to industrial conditions in respect of speed, automation and continues flow has not been possible.

Until now the fundamental resonance frequency at bending and axial vibration, respectively, have been utilized for predication of strength properties. By using information from multi-channel modes a more reliable characterization of the mechanical characteristics of the measured object is obtained.

SE 348 558 describes a non-destructive method that classifies the wood material by exposing the short end of the sample body for a physical hit to generate an energy wave in the sample body. The wave extends in the longitudinal direction. The time for the passage of the energy wave between two sensors is measured and the sample body is classified depending on its coefficient of elasticity, which is determined by the speed of the energy wave and the density of the sample body.

The prior art is also evident through a number of other patent documents. For example U.S. Pat. No. 4,926,691 teaches a method for measuring rigidity and the condition of a wooden structure, preferably poles dug in the ground. The first five resonance modes are used, which are measured by an accelerometer or velocity transducer. U.S. Pat. No. 4,446,733 shows a system for inducing compressive stress in rigid objects for endurance tests. The sample object is held firmly in a holder at a test moment. U.S. Pat. No. 4,399,701 also shows a method for detecting degradation in wood, preferably wooden poles firmly dug in the ground. According to this document, grooves are arranged in the pole for insertion of acoustic transducers in the pole. Two relatively complicated equipments are known through U.S. Pat. No. 5,207,100 and U.S Pat. No. 5,255,565, which require complicated signal processing. U.S. Pat. No. 2,102,614 describes a method for generating and discrimination of vibrations in an airplane propeller. The propeller is suspended by means of an elastic suspension member and a vibrator is connected to the center of the propeller.

SUMMARY OF THE INVENTION

An object of the invention is to provide a method for strength classification of a body, such as wood and other wood-based products in a more accurate, fast and effective way. Another object of the present invention is to provide an industrially applicable technical solution for determination of resonance frequencies of a body for purpose of strength sorting. In a preferred embodiment, the invention can be applied to sample objects, which primarily are continuously and transversely transported.

Experiments have shown that the invention can increase production capacity, for example when classifying wood, about one hundred objects can be classified during one hour compared to the present forty hours.

These tasks have been solved by using a resonance frequency from at least one of the objects natural modes, which resonance frequency is obtained by bringing the object into vibration by means of a stroking body, and essentially controlling the initiation of the movement of the stroking body and following physical impact in time and space through movement of the object. The arrangement according to the invention includes means to bring the object into an essentially free vibration state, a unit for processing collected vibration data and determining rigidity and/or strength of the object alternatively to obtain the geometrical dimension of the object by means of resonance frequencies at least from one of the object's natural modes.

BRIEF DESCRIPTION OF THE DRAWINGS

The invention will be described in more detail with reference to a number of embodiments illustrated in the drawings.

FUNDAMENTAL THEORY

Figure 1A:
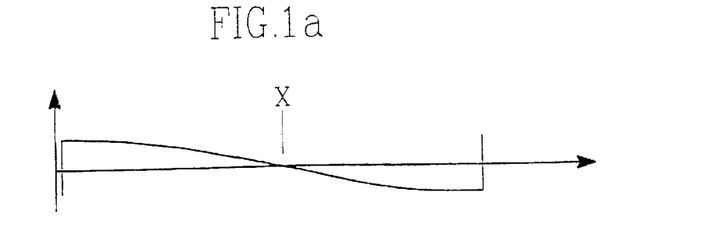
FIGS. 1a–1c are natural modes of axial vibration for a free vibrating object.
Figure 1B:
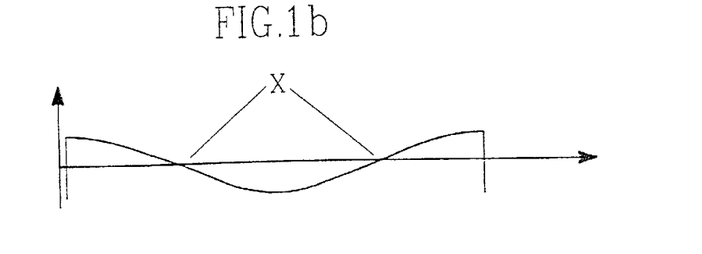
Figure 1C:
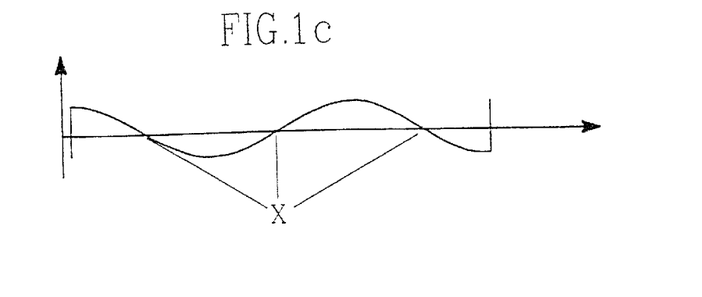
Figure 2:
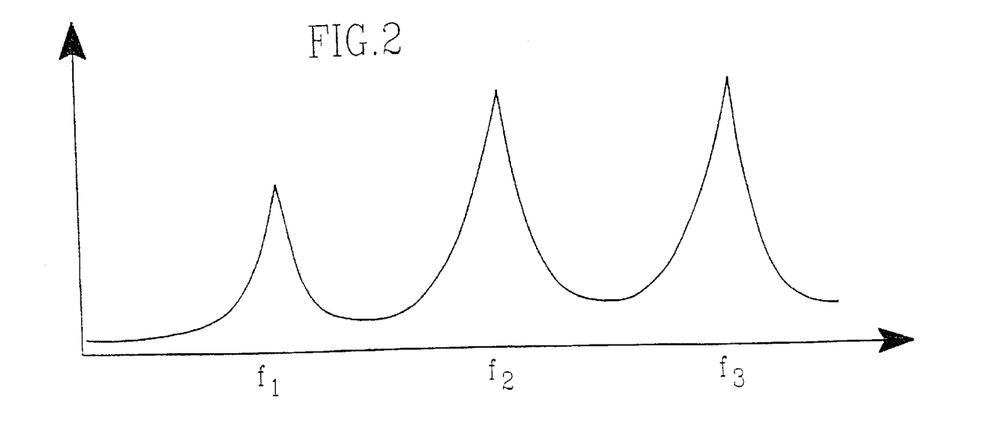
FIG. 2 is an example of a corresponding frequency spectrum for vibration, according to FIG. 1.

If a prismatic body is brought into vibration, for example through a physical impact in the longitudinal direction of the body, different natural modes are identified having specific resonance frequencies $f_n$ and corresponding vibrations. The resonance frequencies of the natural modes and the vibrations are structural properties. No matter where on the body the measurement is carried out, the same resonance frequency for a certain natural mode is obtained. FIGS. 1a–1c show the vibration for some natural modes with axial vibration for a free vibrating object. The vertical axes indicates motion to the left by positive values and motion to the right with negative values. Nodes are zero points in an oscillation and maximums are called antinodes. FIG. 1a shows the natural mode whose resonance frequency is called the fundamental tone; FIG. 1b shows the second natural mode and FIG. 1c the third natural mode. The frequency spectrum in FIG. 2 shows resonance frequencies $f_1$ to $f_3$ belonging to the natural modes shown in FIGS. 1a–1c. The axial vibration implies expansion and compression of the body. The centrum of the body does not move in the first mode. In the second mode, two nodes are obtained where the body does not move and so on. Also, other modes such as flexural and torsional modes occur and can be used.

The resonance frequencies are determined by the geometry of the object, density and elastic characteristics such as coefficient of elasticity E and modulus of shearing G. The resonance frequencies $f_{A-n}$ for different natural modes n for axial vibration of a free vibrating oblong object can be calculated as:

$$f_{A-n} = (n/2L) \cdot (E/\rho)^{0.5}$$

where $f_{A-n}$=resonance frequency for axial mode No. n (Hz)

n=mode number (–)

L=length (m)

E=coefficient of elasticity (N/m$^2$)

$\rho$=density (kg/m$^3$)

A corresponding relationship is found for flexural vibration and torsional vibration. If the resonance frequencies, density and geometry of the objects are definite, the objects coefficient of elasticity can be decided for different natural modes:

$$E_{A-n} = 4 \cdot (f_{A-n} L)^2 \cdot \rho / n^2 \qquad (i).$$

In the same way, the geometry and density can be decided if other parameters are known.

Different parts of a body have different extensions during the vibration depending on the natural mode. At free vibrating axial vibration, for the first natural mode the maximum extensions in the center part are obtained, while the extensions adjacent to the ends become relatively marginal. For the second natural mode, the maximum extensions are obtained in other parts of the object and so on. In the same way, the density of the parts of the object, which moves mainly during the vibration have relatively more importance for the resonance frequency than the parts that move a little, i.e. the nodes. Consequently, for the first axial mode, the coefficient of elasticity of the middle part and the density of the ends decide the resonance frequency of the object. For an inhomogeneous object, in which the coefficient of elasticity varies in the length direction, for example wood, different measured values are obtained for the coefficient of elasticity $E_{A-n}$ depending on the vibration mode. Thus, the differences in the coefficient of elasticity between different modes indicate the degree of inhomogeneity of the object.

The boundary conditions (the reserve conditions) are very important for evaluation of the dynamic characteristics of the object. Well-defined reserve conditions are obtained in a laboratory environment, typically by hanging the object from flexible springs, which simulate a free vibrating condition, so-called free-free suspension. The arrangement can be considered a free-free suspension if the vibrating mass of the springs is small in relationship to the mass of the object and if the fundamental resonance frequency of the system of object-spring is substantially lower than the object's lowest resonance frequency. Other types of boundary conditions are free disposition and fixed clamping. The latter apply for a beam in U.S. Pat. No. 5,060,516.

Sorting of Wood in Respect of Strength

The invention is primarily intended for sorting objects in classes for which specific demands on strength $\sigma_{break}$ and/or coefficient of elasticity E are made. In the present description, an application example of the invention for alternative axial vibration of wood is given, but of course, the principle may be applied to other material and other vibrations.

The primary parameter for strength sorting of wood is bending strength. The criteria for an approved sorting (on the safe side) is that a maximum of 5 of 100 wood pieces may have a bending strength below a value established for each class. Thus, predicting the bending strength of the timber is the most important criterion for comparisons between different machine operations. With a good correlation ($r^2$) between the output of the machine and the bending strength of the timber, a higher share of timber in the higher sorting classes is obtained.

In a laboratory environment it has been shown that connection between the dynamic determined coefficient of elasticity according to the present invention and the bending strength is very good ($r^2$~0.75) compared to conventional static bending sorting machines ($r^2$~0.6). This is described, for instance in "Strength and stiffness prediction using conventional and dynamic methods" by Mikael Perstorper, First European Colloquiums on Nondestructive Evaluation of Wood, University of Sopron, Hungary, Sept. 21–23 1994, vol. 2.

The method according to the invention is primarily carried out by, in the length direction, exposing the wood to be classified for application of a physical impact, which sets the wood in an axial vibration. The resonance frequencies for two or more natural modes are then detected with a sensor. Corresponding elasticity modules are calculated according to equation (i) with knowledge of the density and length of the wood. The wood is assumed to rest on supporting means, which simulates a floating condition. The sorting method is based on axial vibration, for instance, because the boundary conditions are simpler to control for this mode form.

The mean value for coefficient of elasticity from the natural modes that are analyzed, $E_{dyn}$, constitutes the primary parameter for predication of bending strength. This mean value formation implies that a more representative rate of the global coefficient of elasticity of the wood is obtained compared to usage of the first natural mode. The rigidity of the middle part is entirely critical in the latter case while the first case considers the impact of a considerable larger part of the wood.

The difference between the coefficient of elasticity from different natural modes is a measure of the degree of inhomogeneity of the wood and can be part of an independent parameter for an improved predication of the strength. Generally, it is known that low strength wood is more inhomogeneous than high strength wood. Furthermore, the information on an object's degree of inhomogeneity may be of importance for other processes than strength sorting.

The risk for an error in measurement and interference, which could prevent a correct classification, is diminished by over-determination of the coefficient of elasticity. When generating the mean value a control for reasonableness is carried out whereby some natural mode results can be disregarded. Thereby, a more reliable predication and possibilities of error controlling are obtained.

The classification of the wood is carried out according to an established statistical connection between the mentioned mean value generating coefficient of elasticity $E_{dyn}$ and intended mechanical characteristics such as bending strength $\sigma_{bend}$:

$$\sigma_{bend}=A+BE_{dyn},$$

where A is the axial oscillation of the wood and B is a cross-sectional dimension thereof.

Alternatively, direct connection between resonance frequency and strength for an object of given length for different natural modes are used. This is tantamount to using a relevant mean value $\rho_{mean}$ for the sorting group instead of measuring density for each entity.

The density can be measured by registering length, width, thickness and weight or by exploiting established contactless techniques such as x-ray or microwaves. The length and, in applicable cases, also the thickness and width can be decided with a commercially available laser-based technique.

DETAILED DESCRIPTION OF THE EMBODIMENTS

Figure 3:
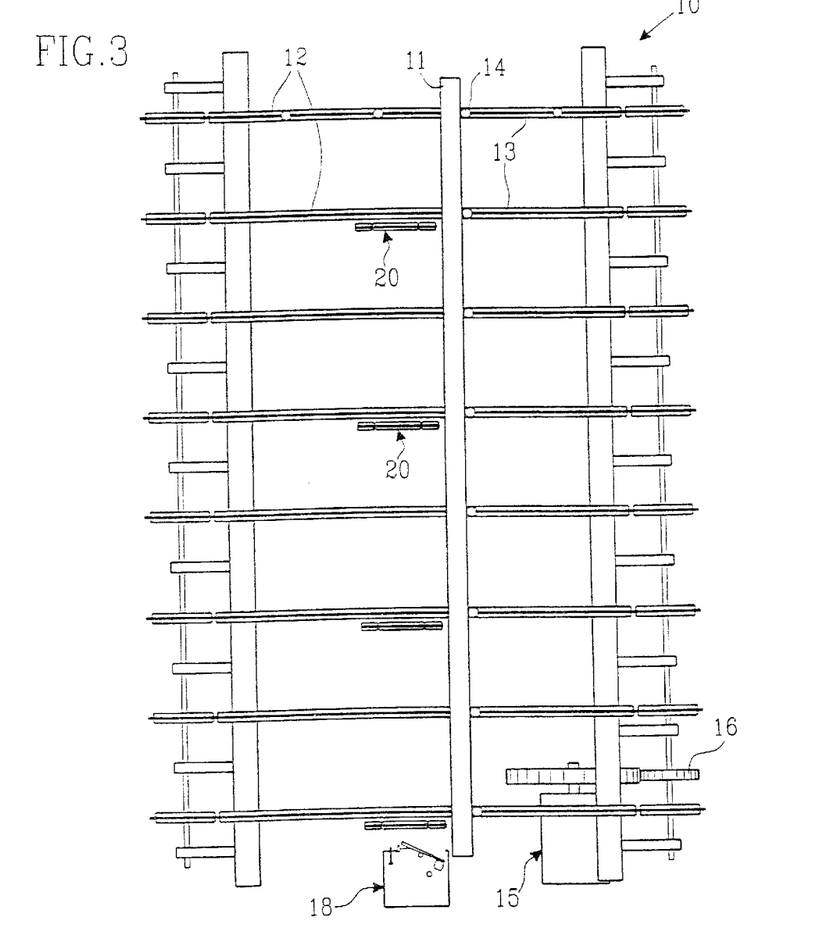
FIG. 3 schematically shows an embodiment of the invention arranged by a typical cross conveyor for wood.
Figure 4:
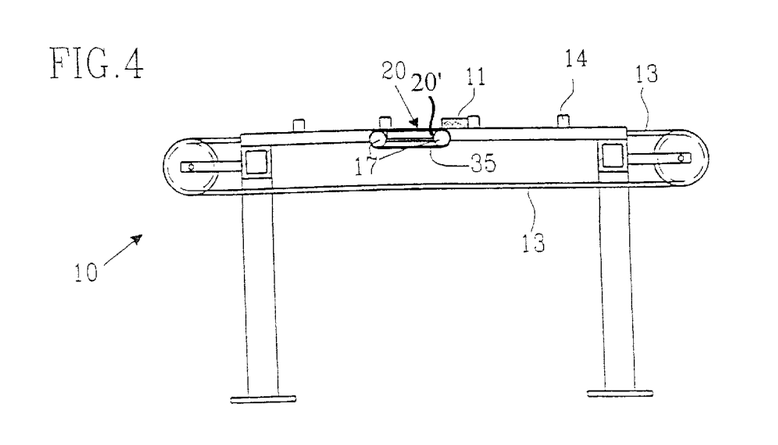
FIG. 4 schematically shows a cross-section through the embodiment according to FIG. 3.

FIGS. 3 and 4 show a first simplified embodiment of an assembly 10, for example in a sawmill, for transportation of the object, in this case timber 11, which is to be classified at a measuring zone for nondestructive classification of the timber. By nondestructive classification is meant a testing operation that does not influence the characteristics of the object. The assembly 10 for instance includes a number of rails 12 on which conveyors in the form of endless transport chains 13 are provided having carriers 14. Driving means in the form of driving assembly 15 and driving wheel 16 are provided to convey the timber 11 to and past a testing unit 18.

The timber 11 is cross conveyed by means of the transport chains 13 with the carriers 14 driving the timber forward continuously. The timber 11 normally rests directly on the chains 13 or slides on the rails 12. The rails (called chain supports) are made for example of steel sections in which the chains run.

The timber 11, whose one end is preferably clearly sawn at an angle without projecting large chips, is manually or automatically placed on the chains 13. As the timber parts can have different lengths, these are placed on the chains so that the timber ends come in contact with the testing unit 18 which lies in the same line. When passing by the testing unit 18, the timber is given a physical impact in its length direction by means of a device shown in detail in FIG. 5. At the impact moment a free vibration condition with respect to the axial vibration is simulated. This is achieved by the timber being brought to rest vertically on a support 20, whose rigidity with regard to vibrations in the longitudinal direction of the timber is low enough and whose co-vibrating mass is low enough.

To simulate a free vibration condition with regard to the axial vibration, the timber 11 can for instance be moved forward resting on the support members which include rubber bands 35 instead of chains or chain supports, e.g., shown in FIG. 4. These rubber bands 35 have plane regions 20'; the levels of which are sufficiently higher than the level of the chains/chain supports, so that vertical bearing is only provided on the bands 35. However, the levels of these plane regions 20' are not so high that the carriers 14 lose contact with the timber. The support members are mounted slightly inclined so that the timber is gradually raised from the chains/chain supports. To guide the timber onto the plane regions and downwards again, the support members can also be provided with inclined slide bars. The rubber bands 35 run in loops and have wheels 17 at both ends. The rubber bands 35 on which the timber rests slide on a surface with very low friction. When the timber 11 is carried up onto the support members via the slide bars by means of the carriers 14, the friction between the timber 11 and the rubber bands 35 is much higher than between the rubber bands and the underlying slide surfaces. Thus, the rubber bands are brought to run along the surfaces. Consequently, the timber does not slide on the rubber bands. The surfaces on which the bands run have edges so that the bands cannot move laterally more than a few millimeters. Thus, the timber is loaded in its longitudinal direction by the impact mechanism without the rubber bands sliding laterally on the smooth track surfaces.

Figure 5:
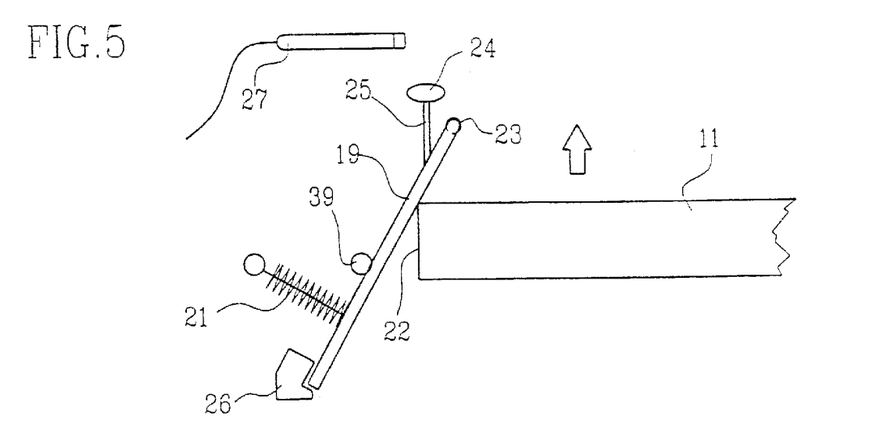
FIGS. 5–7 schematically shows a part of a testing unit according to the present invention and its operation sequence.
Figure 6:
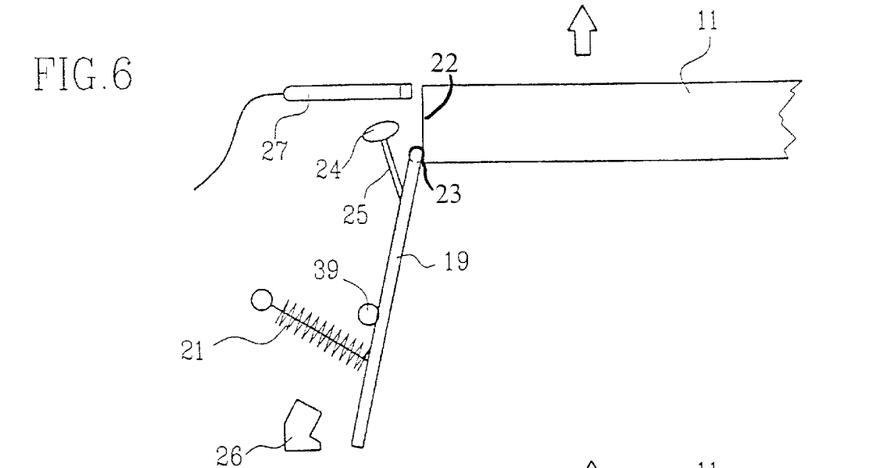
Figure 7:
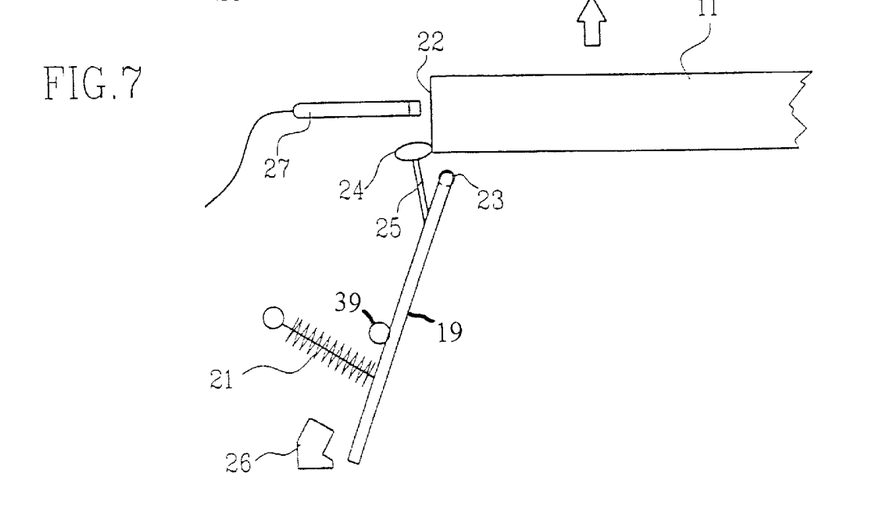

The testing unit 18, according to FIGS. 5–7 includes an arm 19, which can swing in the vertical plane about a pivot or axis 39. When the timber 11 is carried forward in the direction of the arrow, the arm 19 is rotated anticlockwise and a spring 21 is stretched by a corresponding degree. When the timber 11 is carried further forward and reaches the position, according to FIG. 6, the spring 21 is stretched to maximum. A slide spacer or wheel 23 attached to the arm presses against the end 22 of the timber 11. In the next moment, the timber is moved further forward so that the arm 19 loses contact with the end 22 of the timber 11. Thus the arm is turned back toward its rest position by action of the spring force, according to FIG. 7. During this accelerating motion, the end 22 of the timber 11 is encountered by a stroking body 24, attached to the arm 19 via a bar 25. This bar 25 has so low a bending strength with regard to the bending in the plane that the bar 25 and its stroking body 24 has a fundamental resonance frequency smaller than a tenth of the lowest resonance frequency of the sample object at axial vibration. Thus the bar 25 and its stroking body 24 do not generate acoustic pressure with frequency components that can disturb the measurements.

A receiving member 26 is positioned so that the arm at impact does not bear on it. Consequently, at the impact, the spring 21 presses the stroking body 24 against the end 22 of the timber 11 so that the bar 25 is deformed. The high flexibility of the bar 25 results in that the power impulse from the timber piece at the impact is isolated from the arm 19. Thereby, no troubling acoustic pressure is originated from the vibrations in the arm 19 since excitation of the arm is minimized.

A contactless microphone 27 is arranged for recording the emerged sound waves in the timber 11. The microphone 27 is provided so that it, at the impact moment, is essentially in the middle of the width of the timber piece. The microphone 27 is placed so that it, at the impact moment, can collect the radiated acoustic pressure from the end of the timber, originating from the resonance vibrations generated by the impact. An alternative embodiment is to detect the vibration of the object with laser-based sensors. Alternatively, a number of microphones can be arranged in series, if the width of the timber varies, whereby the recording from the most correctly positioned microphone can be used.

The microphone is connected to a computer unit (not shown), the function of which is described hereinafter.

Figure 8:
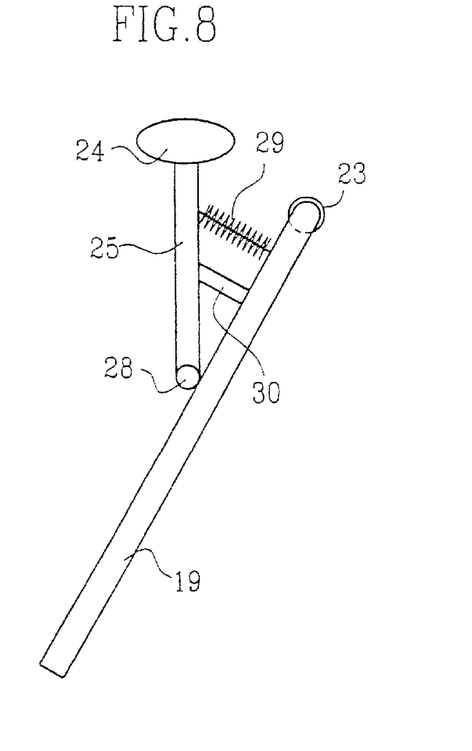
FIGS. 8 and 9 show two additional embodiments of the testing unit according to the invention.
Figure 9:
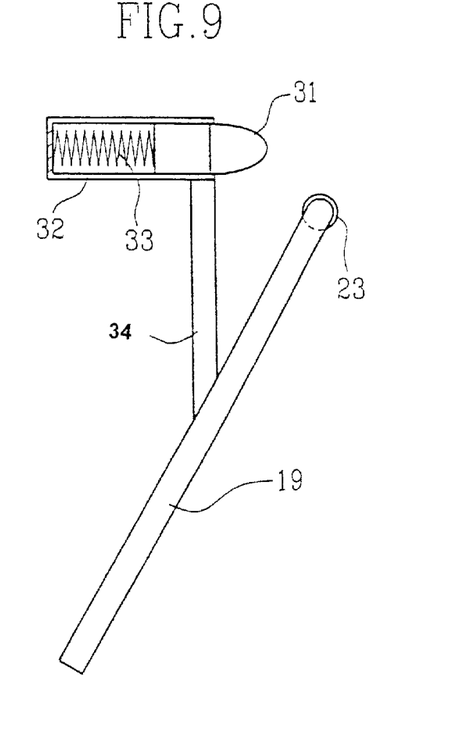

One possible method of achieving the necessary flexibility is shown in FIG. 8 wherein the spring 21, pivot 39 and receiving member of FIGS. 5–7 have been omitted for clarity. In the embodiment of FIG. 8, a stiffer bar 25 via a joint 28 is fastened to the arm 19 and a tension spring 29 provides the flexibility. The tension spring 29 is biased slightly towards a receiving member 30 to ensure the same initial position for the stroking body 24 at each attempt. Yet another embodiment is shown in FIG. 9 wherein the spring 21, pivot 39 and receiving member of FIGS. 5–7 have also been omitted for clarity. In FIG. 9, the cylindrical stroking body 31 is arranged running in a tube 32 with an isolating pressure spring 33 at the bottom. The tube is rigidly attached to the arm 19 via a bar 34.

The mass of the stroking body as well as its geometry and modulus of elasticity with its stop face is, in addition, fitted to the spring rigidity and dimension of the arm and the bar so that the physical impacts generate/excite vibrations having a frequency content that covers the resonance frequencies to be detected.

Another method to avoid exciting the arm is to design the receiving member so that impacts are damped.

Figure 10:
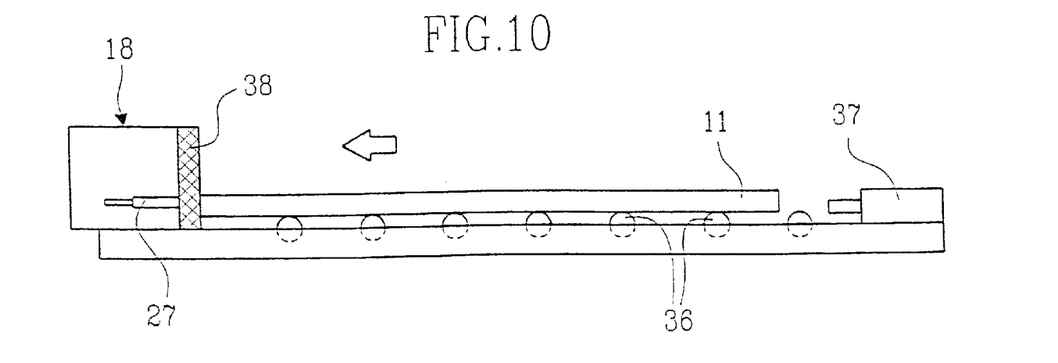
FIG. 10 is a schematic view of a part of another arrangement for classification of bodies according to the present invention.

In the embodiment shown in FIG. 10, the timber 11 is displaced on slide bars or conveying rails 36. Rails 36 are arranged to be rollable or with surfaces having very low friction, at least at the testing zone, i.e., the area that extends in front of the testing unit 18. A stroking mechanism 37, for example a pneumatic motor or a hydraulic piston is arranged at one side of the conveying rails 36. When the timber 11 passes the mechanism 37, it is detected and a compressed air blow displaces the timber laterally towards a rigid impact absorbing body or end stop 38 arranged close to the microphone 27. The collision of the timber with the end stop 38 generates a controlled impact excitation of the timber piece in the axial direction (lengthwise). The frequency content due to the impact is such that the two first axial vibration modes can be excited for all timber pieces to be sorted. The microphone 27 records the acoustic pressure and transfers it to the computer unit. Since the timber length can vary, the stroking mechanism 37 is arranged movable relative to the movement plane of the timber or its impact strength can be varied with regard to the length of the timber so that all timber lengths are given an impact with the same strength.

The assemblies, for example according to FIGS. 3, 4 or 10, are assumed to be located in a sawmill or other wood refining industry as part of the process where the timber is cross conveyed, for instance in a so-called trimmer. In an assembly according to the present invention, a timber piece with a varying length of between 2 and 5m can be classified in the ongoing process during a time period of just one to two seconds.

Generally, the frequency contents in the impacts are such that the first two axial vibration modes can be excited for all timber pieces intended to be sorted. The reflected sound from the end of the timber, recorded by the microphone 27, contains the same frequency content as the frequency content resulting from the impacts. The frequencies that coincide with the two lowest axial resonance frequencies of the timber piece will exhibit strong increased acoustic pressure levels in relation to the remaining frequencies. Also, adjacent frequencies will exhibit high amplitudes.

Figure 11:
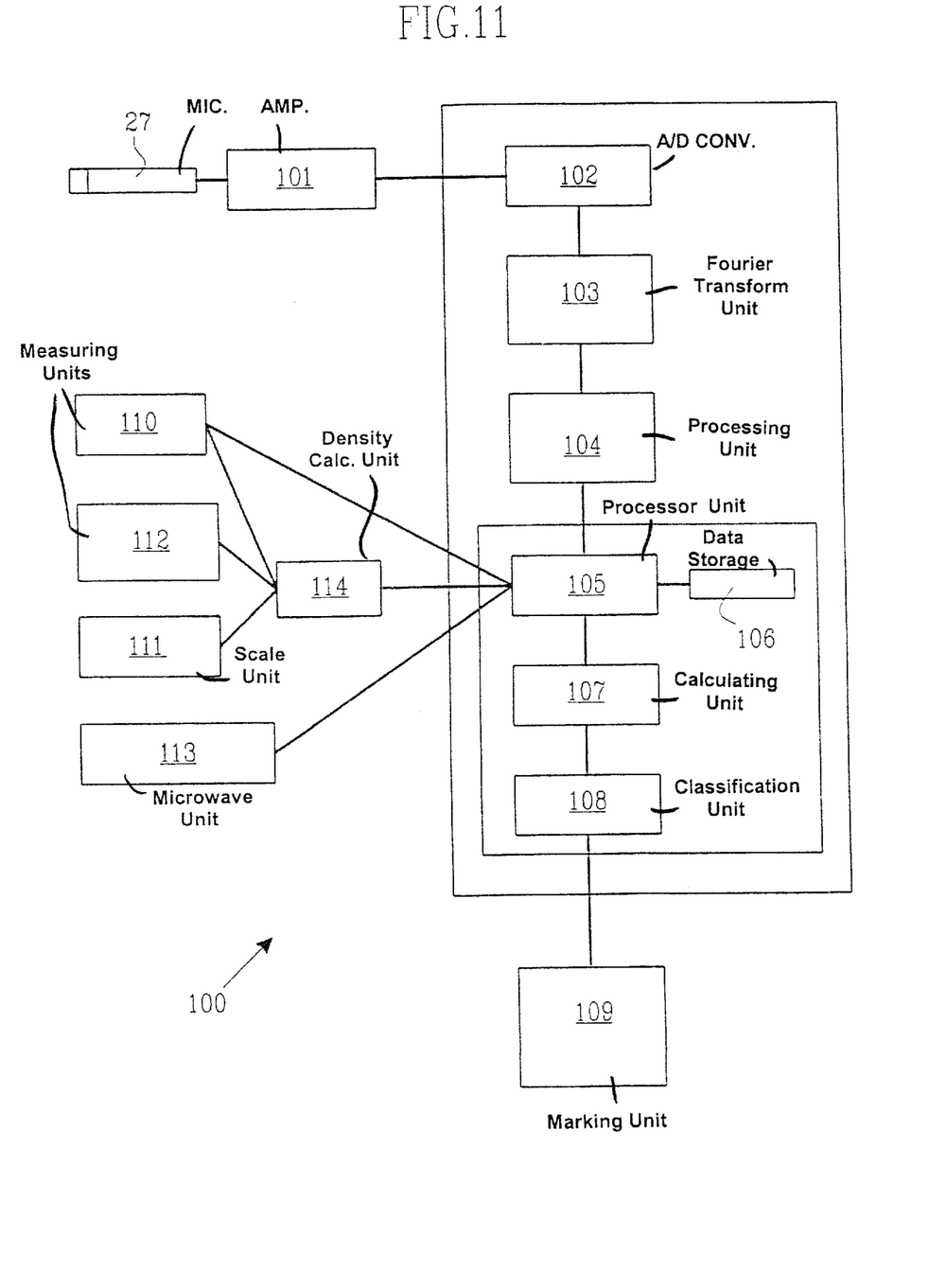
FIG. 11 is an example of a basic function scheme for a control unit for classification of the bodies, according to the present invention.

FIG. 11 schematically shows a block diagram for a computer unit 100, which partly can control the assembly and partly processes the sound received from the microphone.

The sound recorded by the microphone 27 is amplified in an amplifier 101 and the analog response signal in a time unit is converted in an analog-to-digital converter 102 and Fourier transformed in a Fourier transform unit 103 to a digitalized "signal" in the frequency plane, whereby an acoustic pressure spectrum is created by a processing unit 104.

The resonance frequencies in this spectrum can then simply be decided by means of a processor unit 105 which implements algorithm scanning of the spectrum for corresponding high amplitude values. When two actual resonance frequencies have been estimated, the values are compared to reasonable values for actual length, which are stored in a database 106 by the computer unit 100, which manages the measurement and calculation procedure. When said control has been carried out, a mean value is calculated by a calculation unit 107 for the estimated coefficient of elasticity $E_{dyn}$ according to equation (i). By using a statistical connection between the coefficient of elasticity and bending strength the timber piece can be classified in classification unit 108 according to the strength classes that are valid according to standards or other demands in force.

If the standard is changed the classifying value and/or the interval is simply changed in the computer unit 100, which can operate as a control unit of the sorting machine. When the timber piece has been associated with a strength class, the timber piece is marked for ocular inspection and control in marking unit 109.

The machine also generates information for guiding each individual timber piece to the right "line" in a later working moment.

In connection with the measurement of the resonance frequency, also, the information about mass density and timber length are fetched from the computer unit 100.

The timber length can also be determined in measuring unit 110 by means of known commercial laser techniques in close connection with the resonance frequency measurement. The timber piece density can be decided according to one of two alternatives. In the first one, a wave technique is carried out in scale unit 111 and laser-based length measurement are made in measuring unit 112, whereby the mass M and further geometrical cross section dimensions T and B of the timber are obtained.

The other alternative is carried out by means of microwave technology in microwave unit 113, whereby density and moisture ratio, which is a significant parameter for the coefficient of elasticity, is obtained explicitly from density calculating unit 114. However, no "complete" mean values for density are obtained, but a mean value based on one or a pair of points along the timber piece is obtained. These techniques are commercially available.

The moisture ratio may otherwise be assigned an assumed value based on the climatic conditions during a proceeding storage. The length L and the cross section dimensions B and T of the timber are intended to be measured by means of a laser technique, which today is used in several sawmills. The measured data from such commercial equipment is transmitted to the computer unit of the sorting machine. Timber length L is obtained by means of a laser-based length measuring technique.

The marking is carried out so as to be ocularly readable for use and control in later product stages. The assembly can leave information about the sorting result to the computer 100 to enable physical separate storing of the timber in different strength classes after each timber unit leaves the sorting machine. Data storage should partly satisfy the different demands as a basis for statistics and partly satisfy the demands directed by the certifying authorities in connection with reliability control, calibration, etc.

The method can be applied on objects of wood of any length and cross-section. When classifying oblong objects the length can preferably be at least 4 times larger than the cross-section dimensions. The object can be logs of wood, poles, or blocks such as boards, boarding, glulam beams and laminated wood beams. The method can also be applied to I-beams with a rib and flanges of wood or wood-based material.

Instead of contactless microphones, piezoelectric sensors can be used.

Additional Applications

The method and the device according to the present invention can in principle be applied to any rigid, preferably prismatic object to which the theory of elasticity can be applied, such as brick blocks, concrete panels, cement stabilized haydite elements, elements of steel, plastic, gypsum etc., with a view to determining some of the parameters, such as coefficient of elasticity, dimension or density.

In the forgoing description it has been anticipated that the analyses are based on more modes within one and the same type of vibration form. Another method to achieve over-determination of the coefficient of elasticity is to study both the axial and flexural modes. By means of the flexural vibration, the coefficient of elasticity can be decided in a way similar to that used to determine axial vibration. However, to determine flexural vibration, it is required that the cross section geometry of the object be measured exactly.

Usually, the timber has longitudinal, frequently throughout, cracks that originate from timber drying. These cracks, which frequently appear at the ends reduce the capacity to hold against lateral forces on the timber. One can simply say that the shear strength of the timber is low. Existence of these kinds of cracks is consequently important for strength sorting. Presently, educated sorters estimate these cracks visually since no machine is yet found for reliable detection.

By determining the modulus of shearing (G) from torsional vibration, the existence of cracks can be determined. These types of cracks also reduce the torsional stiffness of the object. Thus, a remarkable lowering of the evaluated modulus of shearing of the object is achieved. Low moduli of shearing from torsional vibrations are consequently indicators of the existence of longitudinal cracks.

Moreover, it can be noted that one with the present method can decide the density of the object in a weightless state provided that the coefficient of elasticity, geometry and resonance frequency are known.

Also, the geometrical dimensions for different objects, described above, can be decided through the method according to the present invention.

While we have illustrated and described preferred embodiments of the invention, it is obvious that several variations and modifications within the scope of the enclosed claims can occur.

What is claimed is:

1. An arrangement for the nondestructive determination of at least one property of an object, comprising:
    a conveyer for movably supporting the object;
    a testing unit, including a movable member and a stroking body, mounted adjacent said conveyer, said conveyer bringing the object into engagement with said movable member and then moving the object out of engagement with said movable member whereby, when the object is out of engagement with said movable body, said stroking body physically impacts the object causing the object to freely vibrate at at least one natural resonant frequency mode thereof;
    a detector for detecting the vibration of the object resulting from the physical impact thereon by said stroking body; and
    a computer unit coupled to said detector for processing an output of said detector and determining a property of the object.

2. The arrangement according to claim 1 wherein said movable member is an arm rotatably mounted on a pivot and attached to said stroking body, said arm being rotated about said pivot by movement of the object; and
    a spring having a fixed first end and a second end, the second end of said spring being attached to said arm, said spring being stretched by the rotation of said arm and released when the object is moved past said arm, whereby said stroking body is driven by the force of said spring to physically impact the object.

3. The arrangement according to claim 2 wherein each of said plurality of conveyers is an endless chain, and which further comprises at least one support member adjacent said chain on which the object rests with no vertical movement as it is impacted by said stroking body.

4. The arrangement according to claim 2 comprising
    a rail having a slide surface; and
    a support member including a movable rubber band, said rubber band sliding with relatively low friction on said slide surface prior to said stroking body impacting the object and accelerating when the object comes into contact with said rubber band due to relatively high friction between the object and said band, whereby the object rests on said band without relative motion between the object and said band as the object is impacted by said stroking body.

5. The arrangement according to claim 1 wherein said detector is at least one of a microphone, laser and piezoelectric sensor.

6. The arrangement according to claim 1 wherein the output of said detector is analog data, and said computer unit further comprises:
    an analog to digital converter for converting the analog data to digital data;
    a Fourier transform unit for transforming the digital data onto a frequency plane;
    a processing unit for producing a frequency spectrum from an output of said Fourier transform unit;
    a measuring unit for determining the length, cross-sectional dimensions and density of the object;
    a data storage unit for storing data relating to the object;
    a processor unit for algorithm scanning of the frequency spectrum for resonance frequencies, said processor unit receiving outputs of said measuring and data storage units; and
    a calculating unit for calculating an estimated coefficient of elasticity of the object from measurements of the resonance frequencies, length and density thereof.

7. The arrangement according to claim 1 wherein the object is timber, the length of the timber being at least four time larger than its cross-sectional dimensions.

8. The arrangement according to claim 2 further comprising a receiving member and a tension spring, said receiving member and said second spring connecting said stroking body to said arm, the tension spring being biased toward said receiving member to maintain constant an initial position of said stroking body.

9. The arrangement according to claim 2 further comprising a cylindrical tube having a closed end for receiving said stroking body and an isolating pressure spring, said isolating pressure spring being interposed between the stroking body and the closed end of said cylindrical tube.

10. A method of nondestructively determining a property of an object, comprising the steps of:
conveying the object to a testing unit, said testing unit including a movable member and a stroking body;
engaging said movable member with the object;
moving the object out of engagement with said movable member;
impacting the object with said stroking body thereby causing the object to freely vibrate at at least one natural resonant frequency mode thereof;
detecting the vibration of the object resulting from said impact; and
determining a property of the object from said detected vibration.

11. The method of nondestructively determining a property of an object according to claim 10 wherein said at least one natural resonant frequency mode is from the group consisting of axial and flexural modes.

12. The method of nondestructively determining a property of an object according to claim 10 wherein a property of the object determined from the detected vibration is a modulus of shearing.

13. The method of nondestructively determining a property of an object according to claim 10 wherein said at least one natural resonant frequency mode is measured, and wherein an over-determination is effected by comparing the measured at least one resonant frequency mode with a corresponding theoretical value thereof.

14. The method of nondestructively determining a property of an object according to claim 13 wherein the comparison between a measured resonant frequency mode and a theoretical resonant frequency modes is used as a basis for the determination of a property selected from the group consisting of rigidity, associated strength, geometrical variation of rigidity and non-homogeneity of the object, said determinations being carried out by mean value generation.

15. The method of nondestructively determining a property of an object according to claim 13 wherein the comparison between a measured resonant frequency mode and a theoretical resonant frequency mode is used as a basis for excluding erroneous measurements at a large statistical dispersal of an established rigidity rate determined from different resonant frequencies.

16. The method of nondestructively determining a property of an object according to claim 13 wherein the over-determination is carried out by assuming geometrical variation independency for rigidity of the object.

17. The method of nondestructively determining a property of an object according to claim 10 wherein the vibration of the object is detected by at least one testing device, and said at least one resonant frequency mode is determined by processing in a computer unit.

18. The method of nondestructively determining a property of an object according to claim 10 wherein said stroking body has a motion, form, mass and rigidity which produces said at least one natural resonant frequency mode in said object when impacting thereon.

19. The method of nondestructively determining a property of an object according to claim 10 wherein the impact of said stroking body on said object results from at least one of the momentum of said object and the stretching of a spring.

20. The method of nondestructively determining a property of an object according to claim 10 wherein said object rests during the step of impacting by said stroking body on a support, said support simulating ideal boundary conditions for said at least one natural resonant frequency mode.

21. The method of nondestructively determining a property of an object according to claim 10 wherein said at least one natural resonant frequency mode is determined by automatic scanning of a frequency spectrum produced through Fourier transformation of a vibration of said object and an acoustic pressure response.

22. The method of nondestructively determining a property of an object according to claim 10, said object being freely vibrating, of oblong shape and having resonant frequencies, including the further step of calculating $$f_{A-n} = (n/2L) \cdot (E/\rho)^{0.5}$$

where $f_{A-n}$ = resonance frequency for axial mode No. n (Hz)

n = mode number (–)

L = length (m)

E = coefficient of elasticity (N/m²)

$\rho$ = density (kg/m³).

23. The method of nondestructively determining a property of an object according to claim 10, for flexural vibration and torsional vibration, wherein a coefficient of elasticity for said at least one natural resonant frequency mode of said object is $$E_{A-n} = 4 \cdot (f_{A-n} L)^2 \cdot \rho / n^2$$

where $f_{A-n}$ = resonance frequency for axial mode No. n (Hz)

n = mode number (–)

L = length (m)

E = coefficient of elasticity (N/m²)

$\rho$ = density (kg/m³).

24. An arrangement for the nondestructive determination of a property of an object having first and second opposite ends, comprising:
a conveyer for movably supporting the object;
a testing unit mounted adjacent the first end of said conveyer, said testing unit including an impact absorbing body;
a stroking body mounted adjacent the second end of said object, said stroking body displacing the object on said conveyer to impact the impact absorbing body of said testing unit, whereby the object is caused to freely vibrate at at least one natural resonant frequency mode thereof;
a detector for detecting the vibration of the object resulting from the physical impact thereon by said stroking body; and
a computer unit coupled to said detector for processing an output of said detector and determining the properties of the object.

* * * * *

UNITED STATES PATENT AND TRADEMARK OFFICE
CERTIFICATE OF CORRECTION

PATENT NO.     : 6,347,542 B1
DATED          : February 19, 2002
INVENTOR(S)    : Larsson et al.

It is certified that error appears in the above-identified patent and that said Letters Patent is hereby corrected as shown below:

<u>Column 2,</u>
Lines 25 and 26, change "one hour compared to the present forty hours" to
-- one minute compared to the present forty. --

Signed and Sealed this

Ninth Day of July, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO.  : 6,347,542 B1  Page 1 of 1
DATED  : February 19, 2002
INVENTOR(S)  : Larsson et al.

It is certified that error appears in the above-identified patent and that said Letters Patent is hereby corrected as shown below:

<u>Title page,</u>
Item [73], change "Dynalyze AB" to -- Dynalyse AB --.

Signed and Sealed this

Twenty-ninth Day of April, 2003

JAMES E. ROGAN
*Director of the United States Patent and Trademark Office*